US00PP11553P

United States Patent [19]

Zaiger et al.

[11] Patent Number: Plant 11,553

[45] Date of Patent: Oct. 10, 2000

[54] PEACH TREE NAMED 'SUNLIT SNOW'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 09/197,832

[22] Filed: Nov. 23, 1998

[51] Int. Cl.[7] ..... A01H 5/00

[52] U.S. Cl. ..... Plt./195

[58] Field of Search ..... Plt./195, 196, 197

*Primary Examiner*—Howard J. Locker

[57] ABSTRACT

A new and distinct variety of peach tree (*Prunus persica*); its novelty consists of the following unique combination of desirable features. The following features of the tree and its fruit are characterized with the tree budded on Nemaguard rootstock, grown on Hanford sandy loam soil with Storie Index rating 95, in USDA hardiness zone 9, near Modesto, Calif., and with standard commercial cultural fruit growing practices, such as, pruning, thinning, spraying, irrigation and fertilization:

1. Fruit having a mild, sweet, sub-acid flavor with very good eating quality.

2. Early maturity of the fruit.

3. Heavy and regular production of white flesh fruit.

4. Fruit with firm flesh, good handling and shipping quality.

5. Fruit having a high degree of attractive red skin color.

6. The tree having a vigorous, upright growth habit.

1 Drawing Sheet

ORIGIN OF THE VARIETY

The present new and distinct variety of peach tree was developed by us in our experimental orchard located near Modesto, Calif. as a first generation cross between two selected seedlings with field identification numbers 36EB86 and 5GE8. The selected seedling (36EB86) which was the seed parent, originated from an open pollinated seedling selection that was selected from a cross between May Grand Nectarine (U.S. Plant Pat. No. 2,794) with a peach of unknown parentage. The pollen parent (5GE8) originated from a selected seedling from a cross between Fayette Peach (non-patented) with Royal April Peach (U.S. Plant Pat. No. 3,411) that was crossed with May Crest Peach (U.S. Plant Pat. No. 4,064). A large number of these first generation seedlings grown on their own roots were planted and maintained under close observation and the present variety exhibited the early maturing, white flesh fruit characteristics described above and was selected for asexual propagation and commercialization.

ASEXUAL REPRODUCTION OF THE VARIETY

Asexual reproduction of the new and distinct variety of peach tree was by budding on Nemaguard rootstock, as performed by us in our experimental orchard located near Modesto, Calif., and shows that all characteristics of the tree and its fruit run true to the original tree and are established and transmitted through succeeding asexual propagations.

SUMMARY OF THE VARIETY

The new and distinct variety of peach tree is of large size, vigorous, upright growth and a productive and regular bearer of medium to large size, white flesh, clingstone fruit with very good flavor and eating quality. The fruit is further characterized by having firm flesh with good handling and shipping quality, relatively uniform size fruit throughout the tree, ripening in the early maturing season with a high degree of attractive red skin color. In comparison to the white flesh, Sugar May Peach (U.S. Plant Pat. No. 8,034), the fruit of the new variety is more uniform in size throughout the tree and is approximately 18 days earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large — tree pruned 12 to 14 feet in height and 12 to 15 feet in width at maturity primarily for economical harvesting of fruit.

*Vigor.*—Vigorous — tree growth during first growing season reaches 6 to 7 feet in height and 5 to 6 feet in width. During the first dormant season the tree is pruned 3 to 4½ feet in height when selecting primary scaffolds and to promote proper tree growth for secondary scaffolds to be selected in the second dormant season.

*Form.*—Upright, usually pruned to vase shape.

*Productivity.*—Productive — fruit set is 2 or more times the amount required for normal crop load and fruit is thinned to desired number with proper spacing to develop desirable market size. Number of fruit set per tree varies with climatic conditions during bloom time.

*Bearer.*—Heavy and regular — number of fruit set each spring exceeds normal for desired crop load. Amount of fruit thinning varies with number of trees per acre, soil type climatic conditions and cultural practices.

*Density.*—Medium dense — a1r movement and light are somewhat restricted with the number of branches and leaves growing through the tree. Pruning to open center of the tree (vase shape) is desirable, giving more sunlight to enhance the fruit color, for greater soluble solids (Brix), and to keep fruit wood healthy.

Trunk:

*Size.*—Large.

*Texture.*—Medium shaggy.

*Color.*—Brown to grayish brown (5-E-3) to (5-F-4).

Branches:

*Size.*—Medium.

*Texture.*—Smooth to medium rough, varies with age of growth.

*Lenticels.*—Medium number. Medium size.

*Color.*—Light brown to brown (5-D-6) to (5-E-6), varies with age of growth.

Leaves:

*Size.*—Large. Average length 6 inches. Average width 1½ inches.

*Form.*—Lanceolate, pointed.

*Margin.*—Crenate.

*Thickness.*—Medium.

*Surface.*—Smooth.

*Petiole.*—Medium length — ½ inch. Medium thickness.

*Glands.*—Reniform. Number varies from 1 to 3. Average number 2. Medium size. Positioned on upper portion of petiole and base of leaf blade.

*Color.*—Upper surface — green to dark green (27-D-6) to (28-E-8). Lower surface — dull green to grayish green (27-D-3) to (27-E-3).

Flower buds:

*Size.*—Medium to large.

*Length.*—Medium.

*Form.*—Plump.

*Pubescence.*—Pubescent.

Flowers:

*Size.*—Large, showy. 1¼ to 1½ inches in diameter.

*Pollen.*—Present, self-fertile.

*Blooming period.*—Date of First Bloom: Mar. 1, 1996. Date of Full Bloom: Mar. 7, 1996. Varies slightly with climatic conditions.

*Color.*—Pink to light pink (11-A-2) to (11-A-3). Color fades with age of bloom.

Fruit:

*Maturity when described.*—Firm ripe.

*Date of first picking.*—May 17, 1996.

*Date of last picking.*—May 21, 1996. Varies slightly with climatic conditions.

*Size.*—Medium to large. Average diameter axially 2⅞ inches. Average transversely in suture plane 2⅞ inches. Average weight is 179 grams, varies from 165 to 188 grams.

*Form.*—Globose, nearly rounded. Slightly flattened at stem end.

*Suture.*—Shallow, nearly smooth. Extends from base to apex.

*Ventral surface.*—Nearly rounded.

*Apex.*—Usually slight pistil point, varies from round to slight point.

*Base.*—Retuse.

*Cavity.*—Rounded to slightly elongated in suture plane. Average depth 7/16 inch. Average breadth ¾ inch.

Flesh:

*Ripens.*—Relatively even, only slightly later near stone.

*Texture.*—Firm.

*Fibers.*—Few, small, tender.

*Aroma.*—Moderate.

*Amygdalin.*—Undetected.

*Juice.*—Moderate amount, average Brix 10.1°, sweet, enhances flavor.

*Eating quality.*—Very good.

*Flavor.*—Very good, mild, sub-acid, sweet.

*Color.*—White to pale greenish white near pit cavity (1-A-1) to (1-B-4). Pit cavity — greenish white to grayish yellow (1-B-4) to (1-B-5).

Stem:

*Size.*—Length varies from 3/16 to 5/16 of a inch. Average diameter ⅛ inch. Enlarged at point of fruit attachment Skin:

*Thickness.*—Medium.

*Texture.*—Medium, tenacious to the flesh.

*Down.*—Moderate amount. Medium length.

*Tendency to crack.*—None.

*Color.*—White to yellowish white ground color (3-A-1) to (3-A-3). Nearly overspread with red to madder red (10-C-8) to (10-D-8). Greater enhancement of red color on fruit exposed to direct sunlight then to fruit shaded with little or no direct sunlight. Enhanced red color varies with weather conditions during maturity time.

Stone:

*Type.*—Clingstone.

*Size.*—Medium to large. Average length 1¼ inches. Average width 1 inch. Average thickness ⅝ inch.

*Form.*—Obovate.

*Base.*—Usually rounded, varies from rounded to straight.

*Apex.*—Acuminate.

*Surface.*—Irregularly furrowed toward apex, pitted throughout, heavier toward base. Pit cavities vary from rounded to elongated.

*Sides.*—Equal to unequal. Some stones have one side slightly larger, extending farther out from the suture plane with slightly longer furrows and deeper pit cavities.

*Tendency to split.*—Very slight.

*Color.*—Tan to light brown (7-C-4) to (7-D-5).

Use: Dessert. Market, local to long distance.

Keeping quality: Good — held well in cold storage for 14 days and maintained good firmness and eating quality.

Shipping quality: Good — minimal bruising or scarring in packing and shipping trials.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth and being a regular and productive bearer of medium to large, white flesh, clingstone fruit with very good flavor and eating quality; the fruit is further characterized by having an attractive red skin color, firm flesh with good handling and shipping quality and in comparison to the white flesh Sugar May Peach (U.S. Plant Pat. No. 8,034) has more uniform fruit size throughout the tree and the fruit is approximately 18 days earlier in maturity.

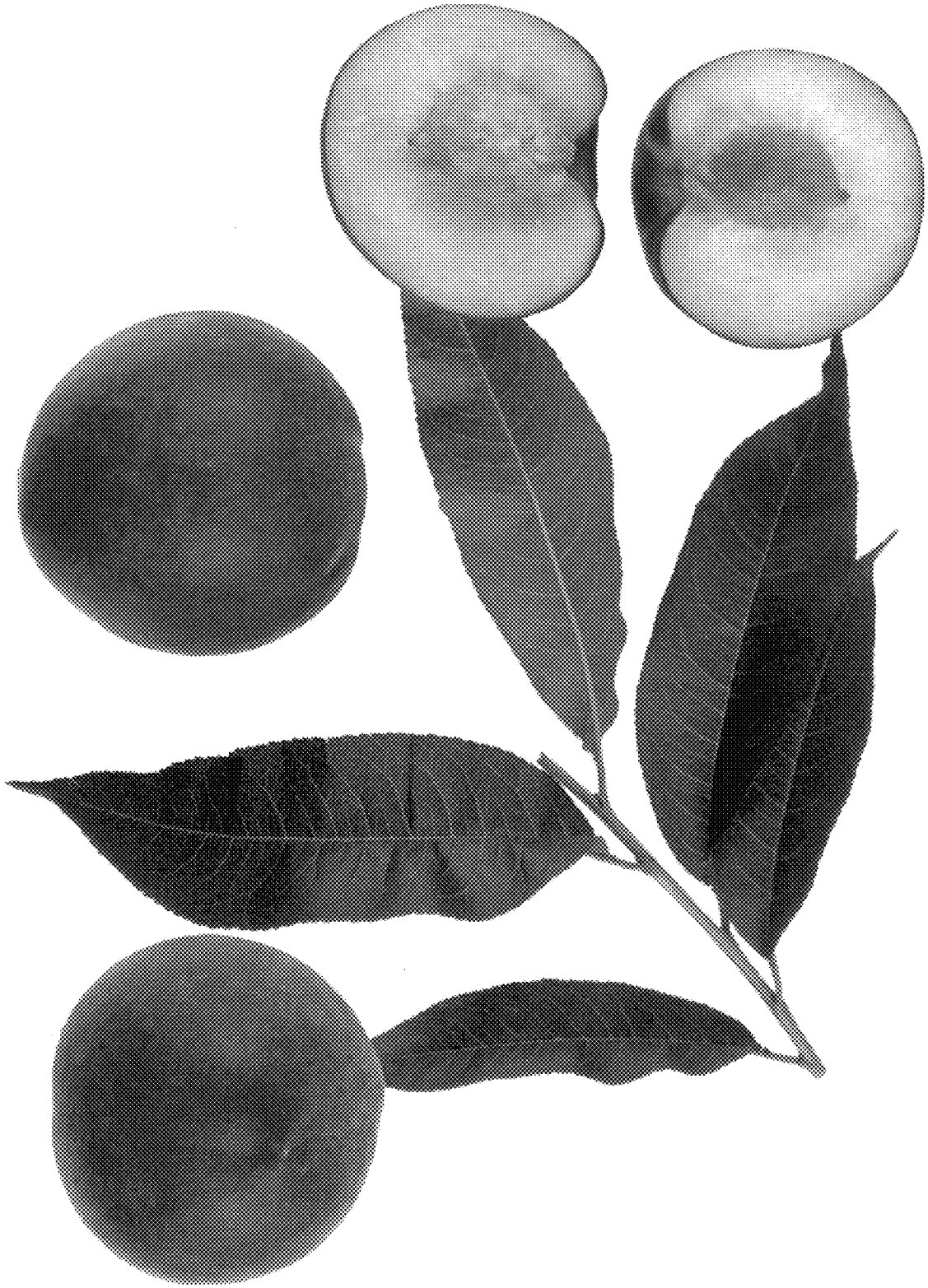

* * * * *